United States Patent [19]

Kroyer

[11] Patent Number: 4,787,883
[45] Date of Patent: Nov. 29, 1988

[54] EXTRACORPORAL THERMO-THERAPY DEVICE AND METHOD FOR CURING DISEASES

[76] Inventor: Karl K. K. Kroyer, 19 Boulevard de Suisse, Monte-Carlo, Monaco, 98000

[21] Appl. No.: 837,688

[22] Filed: Mar. 10, 1986

[51] Int. Cl.⁴ .............................................. A61M 1/03
[52] U.S. Cl. ...................................... 604/4; 604/113; 128/DIG. 3; 210/184
[58] Field of Search ........................................ 604/4–6, 604/113; 210/175, 177, 179, 181, 321.1, 927

[56] References Cited

U.S. PATENT DOCUMENTS

| | | | |
|---|---|---|---|
| 3,881,483 | 5/1975 | Sausse | 604/4 |
| 4,416,280 | 11/1983 | Carpenter | 604/4 X |
| 4,479,798 | 10/1984 | Parks | 604/4 X |
| 4,540,399 | 9/1985 | Litzie et al. | 604/4 |

Primary Examiner—Stephen C. Pellegrino
Attorney, Agent, or Firm—Watson, Cole, Grindle & Watson

[57] ABSTRACT

An extracorporal apparatus for continuously treating the blood of a patient for diseases such as AIDS and cancer includes connectors for removing a flow of blood from the patient and returning the treated flow of blood to the patient, a separator for separating the flow of blood while outside the patient into a first blood flow portion which is enriched in red blood cells and a second blood flow portion which is enriched in white cells, separate heaters for heating the first and second blood portions so as to stimulate the production of white blood cells and antibodies therein and/or attenuate and kill viruses, and a filter for filtering the first and second blood flow portions after they have been recombined.

5 Claims, 5 Drawing Sheets

EXTRACORPORAL THERMO-THERAPY DEVICE AND METHOD FOR CURING DISEASES

BACKGROUND OF THE INVENTION

It is well-known that man is gifted with a system to prevent or overcome diseases. It is the human immune system which reacts against almost every outside influence. If the diseases are caused by weaker bacteria and viruses, the body defends itself using its immune system. Man is not always aware of such a reaction as it does not involve a noticeable rise in the body temperature. It is believed that the body's built-in immune system even reacts against some medicaments administered to the body, for instance antibiotics sometimes cause allergic reactions and have to be withdrawn and are therefore not given the chance to cure which they have proved that they can do in test-tubes (in vitro). Another type of reaction by the immune system occurs when the body is exposed to outside temperatures from, for example, −20° C. to sauna temperatures of more than 50° C., then the immune system reacts to keep the body's temperature normal. However, the body does raise its temperature to several degrees above the normal 37° C. to combat certain bacteria and viruses. During such a rise in temperature (fever), there is a simultaneous production of a higher number of white blood cells, including lymphocytes, or an increase in the power of the existing white blood cells. Such a reinforcement in the strength of the white blood cells is an important part of the natural curing process.

However, there are viruses today which behave in a very different way than normal viruses. AIDS viruses for example, seem, in one way or another, to make the human immune system collapse instead of forming antibodies and vaccines. Therefore it is here believed that AIDS infected patients do not, as a rule, die from the attack by the AIDS virus itself but from other infections because their immune systems have been inactivated by the AIDS virus.

Various types of cancer are notoriously uncurable, they multiply their cells to form malignant tumors. Surgery, x-rays and high-voltage treatment have been used alone or in combination with various medicaments in chemotherapy treatment, however not always with the expected success. For mankind cancer is still a major cause of death.

It is necessary to find other ways of preventing unwanted viruses and cancer cells from being deadly for man.

It is well-known that virus, per se, is labile, notoriously unstable, to even modest temperature increases (i.e., from 37° C. to for example 41° C.). The same instability to temperature also applies to many malignant tumor syndromes—cf, for example, the successful hypothermical treatment of various highly localized bladder cancerous cases (44°/45° C. water treatment of the interior of the bladder).

Virus and tumor cells are severely attenuated by a sudden shift in temperature (for example from 37° C. to 42° C). These findings have been demonstrated by many investigators during the last 10 years, via cell culture experiments (in vitro). For example, it has been demonstrated—by in vitro test-tube experiments—that viruses do not multiply with their usual 37 C rate when exposed to temperatures of 41° C. (ie a 40% reduction of the infectious virus particles was achieved).

A 40% reduction in the ability of a virus to multiply at a rise in temperature of only 3°-4° C. is remarkable. The successful hypothermical treatment of bladder cancers is equally important.

Well-known institutes working in the field of cancer research, in cooperation with hospitals, have published their findings after observing several cases of cancer: malignant cancer tumours completely disappeared in persons who developed a severe fever such as that caused by malaria or smallpox.

Several years ago Dr. Kr Overgaard et al; in cooperation with the research institute for cancer (Kraeftforeningens forskningsinstitut) in Aarhus, Denmark, demonstrated in mice the reaction of cancer tumors to a rise in temperature. A temperature between 41° and 43° C. was created by diathermy. In each case the whole mouse was exposed to the temperature for more than an hour. In 75% of the cases the mice did not survive the rise in temperature. However, in 25% of the cases the mice did survive and the cancer tumors disappeared totally.

An observation made by hospitals seems to be important as it is related to fever situations: If a man is the victim of a coronary infarct he develops (without the presence of any known infection) a fever of about 39° C., 12-24 hours after the attack. A remarkable rise in the number of white blood cells occurs subsequent to the fever.

These findings underline the fact that the white blood cells either increase in number and/or in strength when exposed to temperatures slightly higher than the normal body temperature.

Viruses and cancer cells have a common enemy: a rise in temperature. AIDS viruses and cancer cells are killed or at least severely attenuated at temperatures between 41° C. and 45° C. Low fever stimulates the production of white blood cells and antibodies.

The blood, as it circulates around the body, constantly exchanges substances with the lymph and all other body fluids. The result of this process of exchange has an influence on the spleen, kidneys, heart, liver, marrow, etc, and vice versa. The exchange of lymph, blood and all other body fluids is achieved by osmosis through diffusion and other more direct types of mixing. For example, the thoracic duct daily empties about 2 liters of lymph into the veins of the blood at the junction of the left internal jugular and subclavian veins.

Diminutive quantities of casual intakes of liquid or food, contaminated with heavy metals like lead or mercury, can be measured not only in the blood and bones, but also in the hair. These findings prove that the blood even has an influence on such parts of the body which contain hardly any blood or other body fluid themselves.

SUMMARY OF THE INVENTION

This invention of an extracorporal fever device can be described as a short-term 'bombardment', involving in vitro fever each time the blood passes through the extracorporal device. The fever being produced outside the body might, in some cases, be at a temperature in the extracorporal device which is not acceptable in vivo.

As explained in the beginning of the description of the invention below, an aspect of this invention is that it has the ability to combat viruses, for example AIDS viruses, which have been diagnosed as being present in a person's blood at an early—unsymptomatic—stage, thereby curing a person who is a danger to other people.

If the invention is combined with other features and medicaments, as described later, the extracorporal device can combat more serious diseases, that is diseases further developed (with symptoms) because of AIDS viruses and, for instance, maligant cancer tumours.

Extracorporal devices, for example those used as artificial kidneys, are in daily use all over the world and have probably saved and prolonged the lives of hundreds of thousands of people.

An interesting link has been observed by nephrologists between extracorporal renal dialysis and the absence of AIDS. The following editorial letter (from David N. Edelbaum, MD, FACP) appeared in The New England Journal of Medicine: No AIDS Among Patients on Dialysis?—"I have been intrigued by the apparent rarity of the acquired immuno deficiency syndrome (AIDS) in the dialysis population. One would expect that in such a population—whose members have been invaded by needles and frequent transfusions for many years and have been in a chronic state of immunosuppression—the incidence of AIDS would be much higher than in the general population. The incidence of hepatitis—classic and other forms—is as well documented as those of other viruses—e.g. cytomegalovirus—and all patients on dialysis seem to be susceptible to almost every other infection possible. I have asked many of my nephrologist colleagues about their experience, and they agree that AIDS is almost unheard of in this population . . . . "

If an extracorporal device, used in the treatment of kidney diseases, is able to prevent the development of diseases such as AIDS, then it is easier to understand that this thermo-therapy invention, with its special features including the use of a certain temperature range to stimulate the formation of white blood cells and antibodies, and another, higher, temperature range for the killing of viruses and unwanted cells, and special devices to administer chemotherapeuticals, all working in unison during the blood's regulated reaction time, has the ability to cure.

The invention below described is an extracorporal device, however not only is it used in a very different extracorporal way than those used as artificial kidney or as heart/lung machines, but its construction is also very different as described below.

One aspect of this invention is its ability to cure diseases by connecting an extracorporal thermo-therapy device to the blood vessels, thus providing an extension of the blood's circulatory path by way of a detour through the extracorporal device. This process of passing the blood through the extracorporal device to be repeated as much as up to a hundred times a day, or as little as less than a hundred times a week during the treatment period, combating the viruses and unwanted cells again and again.

THE INVENTION

This extracorporal device, when used to combat unwanted bacteria, viruses and cancer cells, makes it possible to employ a method which does not destroy the body's own immune system but maintains and even enhances it, thereby assisting the immune system in its attack against disease.

This apparatus here described can be called an extracorporal thermo-therapy device providing the beforementioned detour of the blood from its natural circulatory route. While the blood is making such detour it is given an artificial fever treatment. A temporary rise in the temperature of the blood, generated in the extracorporal device, could be 3°–4° C. above a normal body temperature or even several degrees higher than the temperature the body itself can tolerate.

The tendency blood has to coagulate at high temperatures is prevented by adding anticoagulation substances like Natriumnitrate, Heparin, Dextran, etc. Dextran will dilute the viscosity of the blood and, with an addition of saltwater, will secure more distance between the blood cells and the blood plates. Such anticoagulants must be added in quantities sufficient for non-coagulation of the blood at increased temperatures. The anticoagulation effect of Heparin, for example, might be reduced with the right amount of products like proteminosulphate and/or vitamin K, before the blood re-enters the body.

The extracorporal device contains a cooling device which can lower the temperature of the blood to an acceptable body temperature everytime it re-enters the body. Such a temperature could be a few degrees higher than the normal body temperature, thus the blood heated in the extracorporal device creates a fever in vivo thereby enhancing the stimulation of white blood cells and antibodies.

The choice of time and temperature depends on the disease. For example, if during the first hours or days of treatment it is the aim of the extracorporal device to improve the immune system, then the blood will be passed through the detour at a temperature of around 39° C. for a period of time. Once the immune system has improved, the temperature can be increased to one which would attenuate and kill viruses. However, if the aim of the extracorporal device is to start immediately with the combating of viruses and unwanted cells, then a higher temperature will be selected when the treatment commences. Once a cure has been set in motion, the temperature can be lowered several degrees to one which would improve the immune system.

The extracorporal device allows for a choice to be made in the temperature—for example 3 days at a temperature of 39° C. and 3 days at a higher temperature of 43° C. In addition the device allows for such sequences of temperature to be repeated several times, depending on how far the cure has progressed.

The device, in accordance with the invention and the method in accordance with the invention, is in one special embodiment executed in such a way that the blood coming from the veins of the person is separated so that one portion of the blood contains the majority of white blood cells plus serum, while the other portion of the blood contains predominently red blood cells plus serum. This separation enables the blood which contains mostly white blood cells to have a different treatment in time and in temperature compared to the one which the other portion of the blood receives at the same time. The advantage of such a separation is that it is possible to keep the blood containing the white blood cells outside the body for a longer time and at a temperature of, for example, 39° C., thus improving the white blood cells' power and the blood's immune system. The portion of the blood which contains more red blood cells might be treated with a higher temperature, for instance a temperature in the order of 42°/43° C.

The temperature range which preferably should be used in the extracorporal devices where the blood is running in a single detour or a parallel detour is from around 2° C. higher than normal body temperature to a degree around 2° C. higher than high fever body temperature.

It is to be understood that in one embodiment the invention, as described, has a battery of several extracorporal reactor devices to be shunted in or out, thereby making it possible to run the equipment with different blood temperatures. In this way it is possible to have a detour with a blood temperature of, for example, 39° C. in some of the reactors and to have a temperature of, for example, above 40° C. in other reactors of the extracopral device.

In one embodiment of the invention a reactor can is involved in the process. The purpose of the reactor can is to prolong the treatment period of the blood or part of the blood. The can is preferably positioned after the extracorporal device so that the blood passes through the extracorporal device and the reactor can successively, before re-entering the body. The level in the reaction can to be regulated by keeping the can more or less filled up with blood, for example with from 100 ml to 1 liter or more.

In another special embodiment of the reactor can, the can has plates placed from the top of the can from one side to another. The first plate is fastened to one side of the can in a declining position, not touching the other side of the can. The next plate is placed in a declining position opposite the first plate and is connected to the other side of the can. This plate system is repeated several times in a downward direction in the can. The plate system in the can is intended to improve the oxidation of the blood, by running it in thin layers over the plates. The can and its plates will also ensure that the blood which enters the reaction can first will also leave first, via the bottom of the can.

In the above-mentioned reactor can chemicals, pharmaceuticals, antidotes, protein sulphate, etc, can be checked and regulated to the maximum level for the patient and his disease. In the reactor can it is also possible to regulate the temperature of the blood, according to which of the following treatments are to be employed: the enhancing of the immune system and/or; the combating of viruses and unwanted cells.

Virus-attenuating pharmaceuticals can also be added, according to the invention, while the blood is on its detour through the extracorporal device and the reaction can. An example of such a pharmaceutical is Formaldehyde which is added, via the extracorporal device, to the blood in very small quantities (preferably in vapour form) while it is on its detour. Formaldehyde can be dangerous when added to the human body itself, however it is not dangerous when added in such small quantities to the blood in vitro. The Formaldehyde is used in vitro to change dangerous viruses into corresponding vaccines. Formaldehyde changes poisonous toxin into antoxin thereby keeping or even producing active antibodies in the blood.

It is possible to operate the reaction can in such a way that ultraviolet light or light of the wavelengths of natural sunshine can be directed to the blood while the blood is splashing from one of the can's declining plates to another. Ultraviolet light is a killer or attenuater of many viruses. Ultraviolet light can be exposed to a higher quantity of blood in the reaction can than sunshine is by reaching a person's skin. Ultraviolet light is used for attenuating and/or killing viruses to produce vaccines, for instance against poliomyelitis.

The administration of certain very active pharmaceuticals is a possibility because antidotes and other neutralising agents can be used to reduce the level of pharmaceuticals to a level which will not cause harm to the body, before the blood re-enters the body. In this way the blood receives a treatment outside the body from which the patient benefits in vivo.

It is here believed that another advantage of keeping a portion of the blood, for instance half a liter or more, out of the body while it is on the detour through the extracorporal device, is that this process, independent of any other treatment the blood receives on the detour, will improve the blood's ability to heal. This belief follows the theory of phlebotomy by which the newly formed blood cells and antibodies etc are of a "quality" superior to those which have been temporarily taken out. This blood-letting system, combined with the invention's low-fever method, enhances the body's immune system.

When the treatment period is over, after hours or weeks, the blood contained in the extracorporal device and the reactor can might go back to the body via a small osmotic dialysis unit which is used to remove a surplus of water and other substances in accordance with the opinion of the medical supervision. An alternative way to remove a surplus of water is to administer diuretics.

Using diathermy to heat the blood passing through the extracorporal devices is an alternative to heating the blood using water or other liquids surrounding the blood contained in the extracorporal devices. Diathermy is supposed to minimise blood clotting or adherence to the apparatus.

An instantly-working analysis equipment connected to the extracorporal device and to the body, monitors the effect of the treatment on the patient's general condition, in the first instance to evaluate how strong a treatment (temperature, time, medicaments, etc) the patient can tolerate, in order to bring about a cure as soon as possible and in the second instance to correct any undesired effect on the patient's condition.

As mentioned before, temperatures around 39° C. are mainly for improved formation of the body's antibody and immune system, and temperatures above 40° C. are mainly for attenuating, by repeatedly combating viruses and unwanted cells and bacterias until they have been annihilated.

The vital organs of the human body benefit from the treatment which the blood receives on its detour, because they are connected to the body's circulatory system of which the extracorporal device, according to the invention, is an integral part. Everytime the blood returns to the vital organs the blood has improved in quality, and thereby in its ability to cure.

It is obvious that a greater effect will be obtained by using a continuous extracorporal thermo process, according to the invention, rather than a process which is discontinued, i.e., a batch process.

Therefore, it is an object of the invention that not enough time should be allowed for already attenuated viruses and unwanted cells to recover or multiply. These invaders should be attacked again and again until a cure is achieved.

From the dialysis column the blood enters an instantly-working analysis equipment 37, to check the condition of the blood on its detour, and the condition of the patient, and then the blood enters a pumping and pulsator system 38, from where the blood, now treated, re-enters the body of the patient at connector 39. From the pumping system 38 there is another possible outlet through a valve system, also contained in 38, through a tubular system 40, which can deliver a portion of the treated blood to another part of the patient's body.

Figure 1:
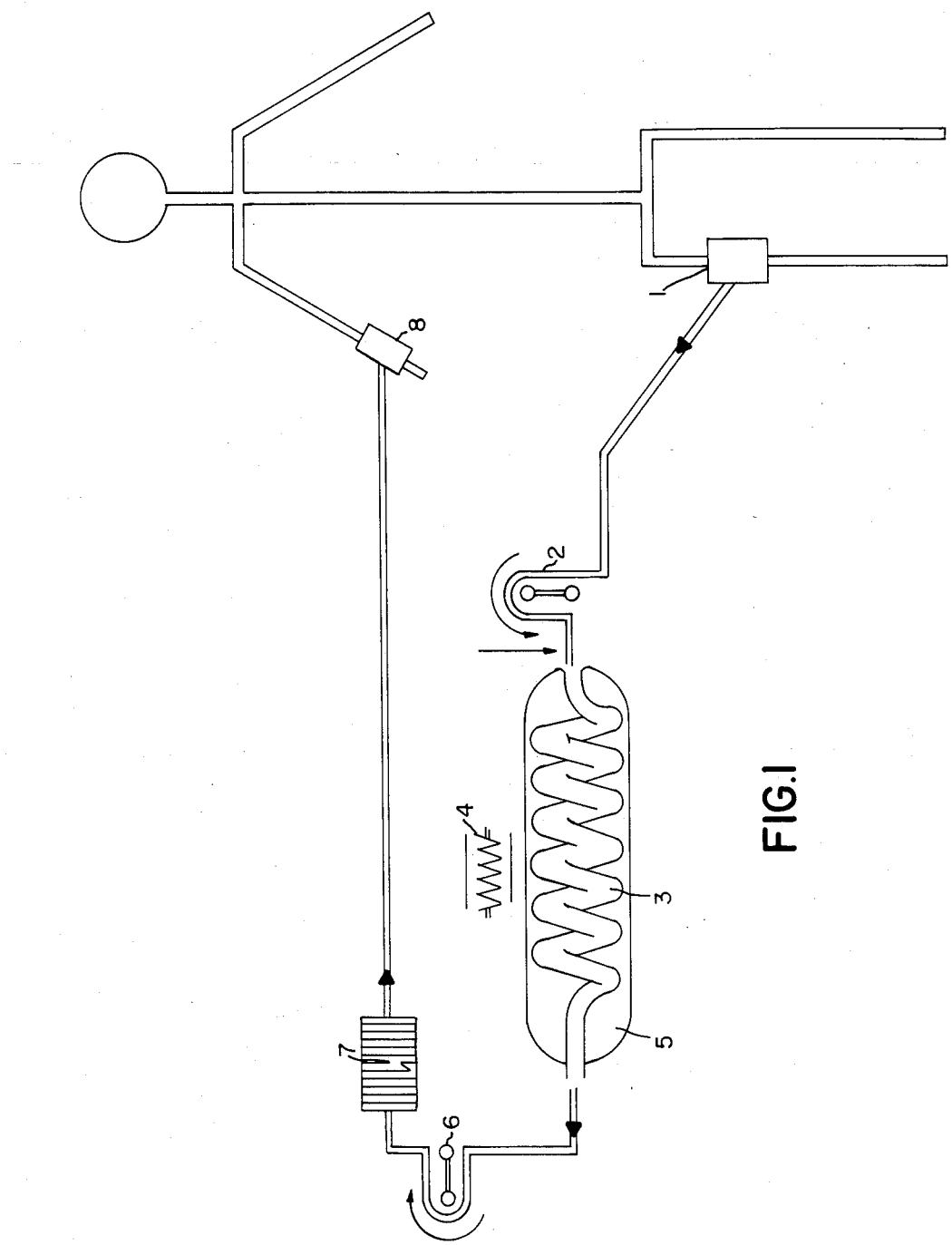
FIG. 1 shows a first preferred embodiment of extracorporal apparatus according to the present invention. It includes a connector 1 which is connected to a patient's blood vessel a pump 2, an extracorporal device detour reactor 3, which is heated by means of 4, being equipment for diathermy heating, or else, a fluid system 5 for raising the blood temperature on its detour. The blood continues through another pump 6, which for pulsation purposes may be out of rhythm with the pump 2. From the pump 6 the blood passes a filter 7, which prevents possibly clogged particles of the blood re-entering the body, and then back into the patient at connector 8.
Figure 2:
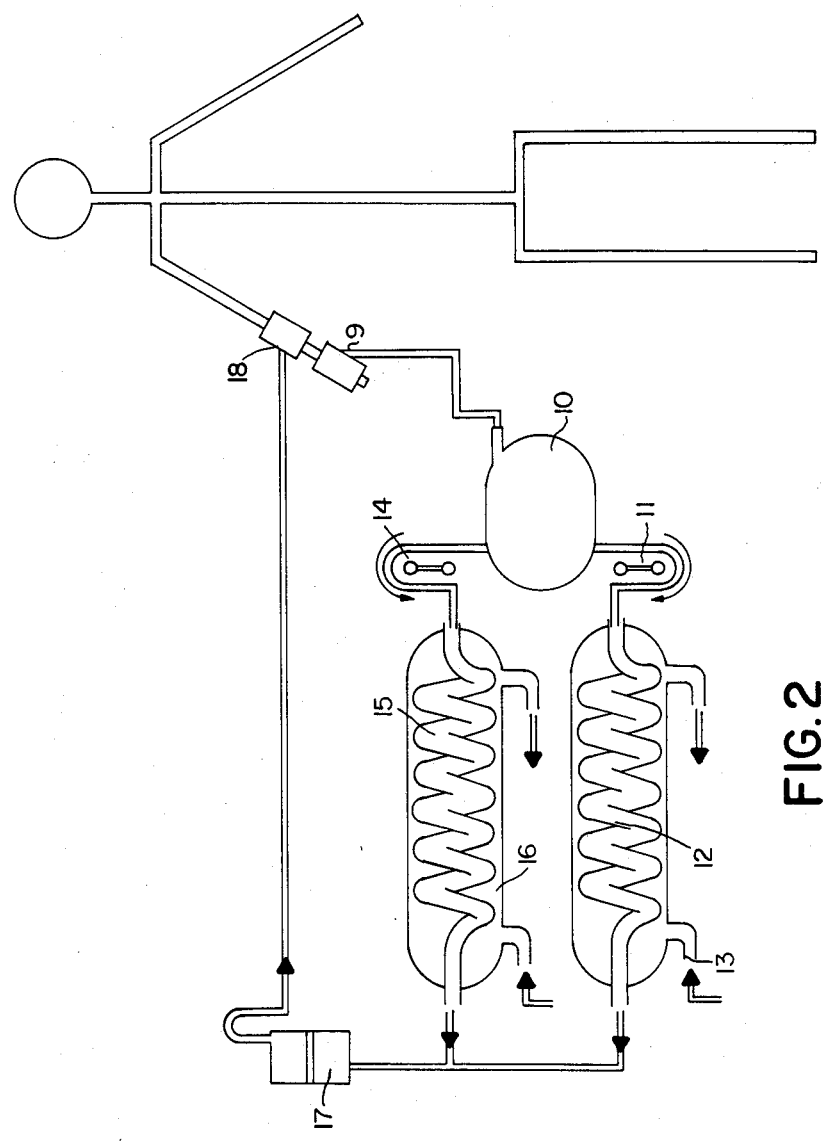
FIG. 2 shows a second preferred embodiment of the invention. It includes a connector 9 which is connected to a patient, a separator 10 for separating the blood supplied thereto from connector 9 into two portions— one being richer in red blood cells and the other being richer in white blood cells. From the separator, one outlet of the blood is passed through a pump 11 to the extracorporal device detour reactor 12, which is heated by surrounding liquid 13. The other portion of the blood from the separator 10 is passed through another pumping system 14 from which it is led to a parallel extracorporal device detour reactor 15, which is heated by surrounding liquid 16. The two portions of the blood are both then led to a filter 17, before the blood re-enters the patient's blood vessels via connector 18.
Figure 3:
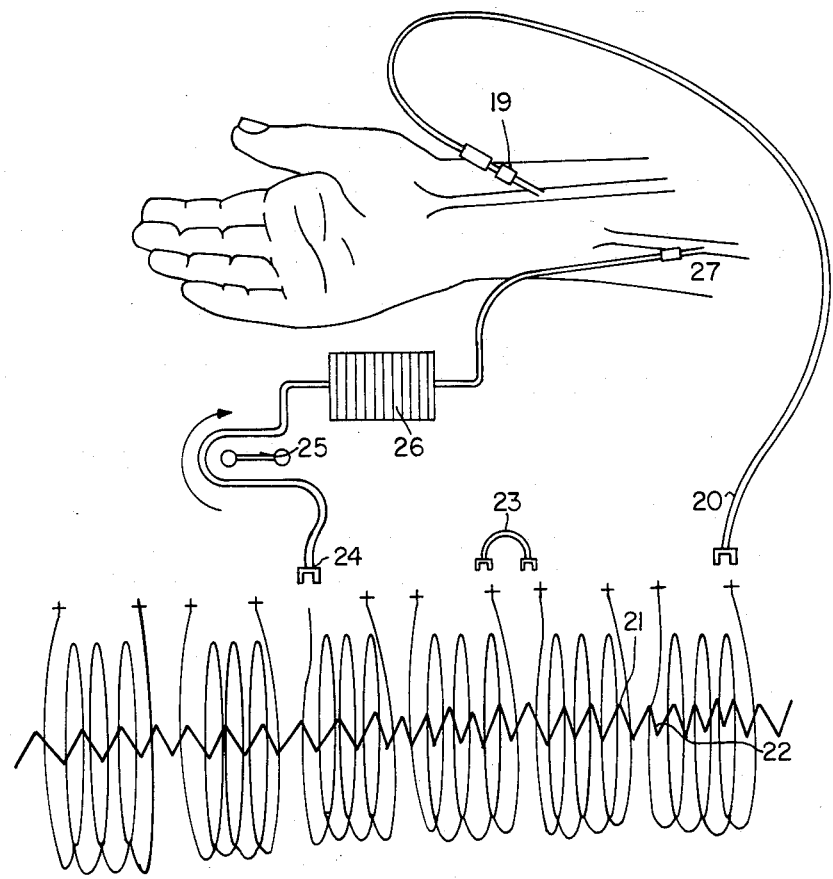
FIG. 3 shows a third preferred embodiment of the present invention. It includes a connector 19 connected to a patient's blood vessel, which is connected to a tubular system 20 which leads the blood stream to one or several of the battery of reactors 20, heated by electricity, preferably diatherm 22 through tubes with fittings 23 which enable the insertion of several reactors to keep the blood on its detour for an extended time. A fitting 24 connects the blood to a pump 25. The blood passes through a filter 26 and then returns to the veins of the patient at connector 27.
Figure 4:
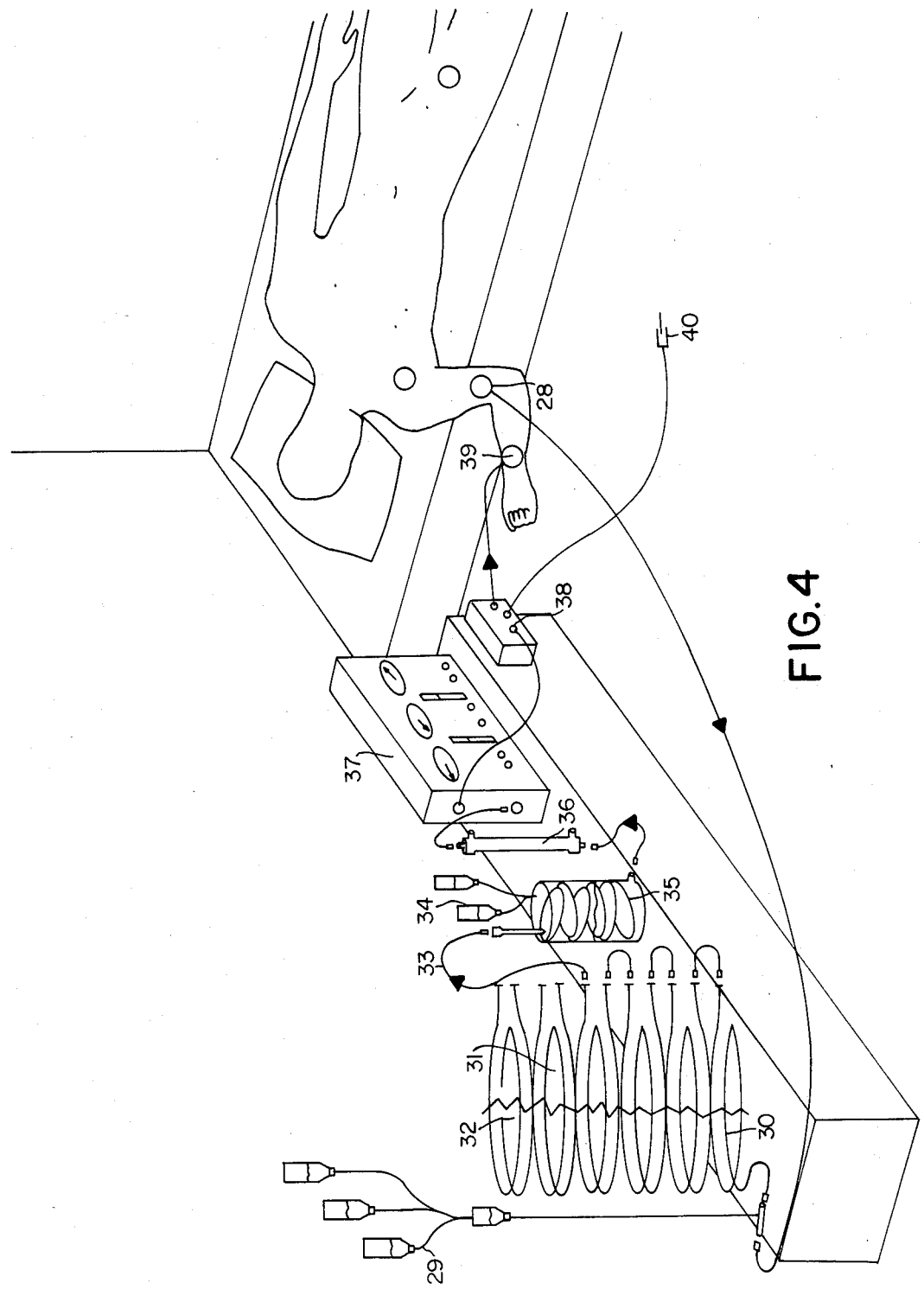
FIG. 4 shows a fourth preferred embodiment of the present invention. It includes a connector 28 which is connected to a flow circuit which includes patient's blood vessel, a series of supply bottles 29 for adding various medicaments, pharmaceuticals and chemicals, including Interferon and Interleukin, etc, to the flow of blood before it enters a tubular detour reactor 30. Other reactors 31 to be shunted in or out depending on the desired reaction time. A is the heating system 32 is employed to control the temperature rise of the blood in the detour reactor and a connection 33 extends between the detour reactors and a reactor can 35 to which it is possible to add other medicaments which may increase or reduce the effect of the medicaments added by supply bottles 29. The reactor can 35 retains a portion of the blood to increase the reaction time and has plates to make the blood pass in thin layers if desired. Supply bottles 34 can be used to administer pharmaceuticals, chemicals and/or antidotes to the blood. The reactor 35 can be open or closed as desired. A dialysis column 36 can be used, according to the invention, to clean the blood after the blood has passed a filter, (not shown on this drawing).
Figure 5A:
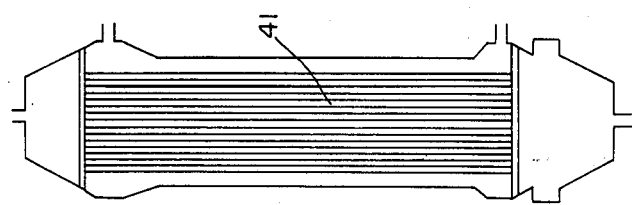
Figure 5B:
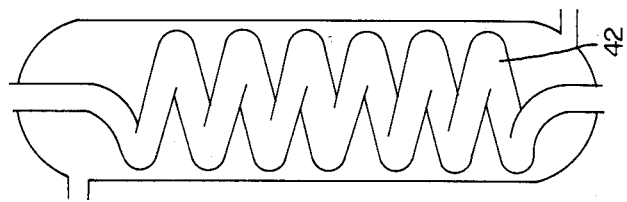
Figure 5C:
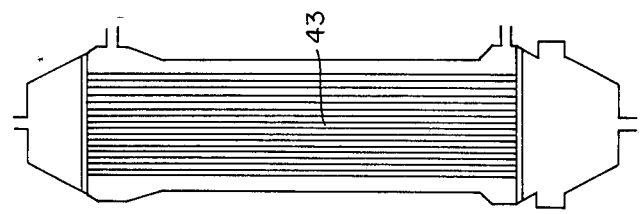

FIGS. 5a-5c are to be understood in relation to FIGS. 1, 2, 3, 4 and the corresponding explanation of these figures. However, FIGS. 5a-5c illustrate embodiments of the invention, which are neither too complicated to administer in medical care, nor too inconvenient for the patient. In these Figures valves, pumps, analysis equipment, medicament supply, are not shown.

FIG. 5a shows one of the preferred embodiments of the invention: The blood enters a dialysis osmosis apparatus 41 of the type conventionaly used as artificial kidneys. However, in accordance with the invention, pharmaceuticals and chemicals are to be administered through an osmosis process into the blood, the dialysis liquid surrounds the tubes in the dialysis equipment, thereby delivering the pharmaceuticals and chemicals to the blood. FIG. 5b shows the thermo-therapy reactor 42, itself heated by diathermy or liquid such as water.

FIG. 5c shows a second dialysis device 43, which through osmosis—or reverse osmosis removes, regulates or controls the blood and the medicaments added, before the blood re-enters the body of the patient.

A raised temperature in the dialysis equipment 41 and 43 adds reaction time, if preferred, to the blood beyond the reaction time secured in the reactor 42.

I claim:

1. An extracorporal thermo-therapy apparatus for use in continuously treating the blood of a patient for disease, said extracorporal apparatus comprising
   first connector means for removing a flow of blood from a patient,
   second connector means for returning said flow of blood to said patient, and
   a flow circuit connected between said first connector means and said second connector means, said flow circuit including
      a separator for separating said flow of blood into a first blood flow portion which is enriched in red blood cells and a second blood flow portion which is enriched in white blood cells,
      a first heating means for raising the temperature of said first blood flow portion,
      a first pump for moving said first blood flow portion through said first heating means,
      a second heating means for raising the temperature of said second blood flow portion,
      a second pump for moving said second blood flow portion through said second heating means, and
      a filter for filtering said first and second blood flow portions after they have been recombined.

2. The extracorporal thermo-therapy apparatus according to claim 1, wherein at least one of said first and second heating means comprises a helical tube through which the associated blood flow portion flows and a casing surrounding said helical tube, said casing including an inlet for enabling heated fluid to enter said casing and surround said helical tube and an outlet for removing heated fluid from said casing.

3. A method of treating a patient for disease, said method comprising the steps of
   (a) withdrawing a continuous flow of blood from the patient,
   (b) separating said flow of blood into a first blood flow portion which is enriched in red blood cells and a second blood flow portion which is enriched in white blood cells, (c) separately heating said first and second blood flow portions, (d) combining said heated first and second blood flow portions, (e) filtering said combined first and second blood flow portions, (f) cooling said combined first and second blood flow portions, and (g) returning said combined first and second blood flow portions into said patient.

4. A method according to claim 3, wherein in step (c) said first blood flow portion is heated to a higher temperature than said second blood flow portion.

5. A method according to claim 4, wherein in step (c) said first blood flow portion is heated to between 42° and 43° C., and said second blood flow portion is heated to about 39° C.

* * * * *